United States Patent [19]

Valdespino et al.

[11] Patent Number: 4,736,750
[45] Date of Patent: Apr. 12, 1988

[54] APPARATUS FOR TESTING PULMONARY FUNCTIONS

[76] Inventors: Joseph M. Valdespino, 5023 Golf Club Pkwy., Orlando, Fla. 32808; William M. Hobby, III, 244 Sylvan Blvd., Winter Park, Fla. 32789

[21] Appl. No.: 256,985

[22] Filed: Apr. 24, 1981

[51] Int. Cl.$^4$ ............................................. A61B 5/08
[52] U.S. Cl. ................................. 128/725; 73/861.21; 73/861.03
[58] Field of Search ............... 128/725; 73/861.63, 73/861.64, 861.61, 861.21

[56] References Cited

U.S. PATENT DOCUMENTS

| | | | |
|---|---|---|---|
| 2,112,441 | 3/1938 | Lewis | 73/861.63 |
| 2,669,876 | 2/1954 | Lentz | 73/746 X |
| 2,841,667 | 7/1958 | Stowe | 73/861.63 X |
| 3,621,835 | 7/1969 | Suzuki et al. | 128/725 |
| 3,703,893 | 11/1972 | Hardway | 128/725 |
| 3,924,612 | 12/1975 | Dempstor et al. | 128/725 |

FOREIGN PATENT DOCUMENTS

| | | | |
|---|---|---|---|
| 2928568 | 1/1981 | Fed. Rep. of Germany | 73/861.21 |
| 884231 | 12/1961 | United Kingdom | 73/861.21 |

*Primary Examiner*—Edward M. Coven
*Assistant Examiner*—J. Hanley
*Attorney, Agent, or Firm*—William M. Hobby III

[57] ABSTRACT

An apparatus for testing pulmonary functions uses a hollow tube having a venturi therein and an aspirator orifice in the hollow tube adjacent the venturi. A pressure signal analogous to the flow of air through the hollow tube is generated in the aspirator orifice. Various means are provided to respond to the pressure at the aspirator orifice and a timed cut off of the aspirator orifice is provided for measuring the flow for a predetermined time period, such as one second, thereby indicating the forced expiratory volume for one second (FEV$_1$) without having to blow into expansible chambers, such as bellows or bags to determine the volume of air passing through the tube. The apparatus is adapted to measure the total volume of air passing through the tube, or the total volume during a predetermined time period. Timed cut off of the aspirator orifice is accomplished by both mechanical and electrical means and the measuring of the aspirator orifice pressure is accomplished either with a liquid column or with an enclosed variable volume chamber, having electrical or mechanical indicators to determine the position of the reduced volume in the chamber.

50 Claims, 3 Drawing Sheets

APPARATUS FOR TESTING PULMONARY FUNCTIONS

BACKGROUND OF THE INVENTION

The present invention relates to testing of pulmonary functions and more specifically to the measurement of the forced expiratory volume for one second ($FEV_1$) and the forced vital capacity (FVC).

Determining and detecting lung function failure, such as various types of emphysema, is presently an established practice to use various types of spirometric examinations, in which the vital capacity and forced expiratory volume at predetermined intervals are measured for comparison with given values. The presence of a failure in the lung function is detected through comparison of the subject's vital capacity with theoretical values which are dictated by the sex, age and height of the subject. The extent and type of the failure can be determined by correlation between the vital capacity and the time forced expiratory volume. When determining respiratory function, a medical practitioner may use a number of criteria for determining the condition of the patient. Two often used criteria are the forced vital capacity (FVC) of the patient's lungs and their forced expiratory volume timed for one second ($FEV_1$). The ratio of these two volumes ($FEV_1/FVC$) is also used for diagnostic purposes. In normal patients the ratio of $FEV_1/FVC$ is greater than 75% (0.75). A ratio of less than 75% is indicative of an obstructive impairment, such as asthma or emphysema.

Typical prior art spirometers use an expansible chamber in which the patient exhales. A scale measures the expansion of the chamber to determine the volume exhaled. Chambers can be a bellows-type or a bag having graduations marked thereon, which after exhaling into, can have the air pushed to one end to determine the volume exhaled into the bag. Another technique used in spirometers include hot wires in which resistance is varied in accordance with the cooling of the wire by air being blown through a tube. More commonly, a flow meter is used having rotating vanes rotated by a patient's breath being blown through the vanes thereby rotating the vanes. In order to measure the $FEV_1$, a determination of the volume of air exhaled in the first second must be known and therefor must be timed in some manner. A commonly used spirometer uses an expansible chamber into which the patient exhales driving a pen over a clock driven chart calibrated so that a one second period can be determined. Such an instrument is bulky and expensive and requires readings to be taken from the chart. Accordingly, physicians are apt not to test pulmonary functions during routine examination. It has also been suggested to cut off the breathing tube in a spirometer after one second, but this sudden cut off might have adverse consequences for some patients.

One advantage of the present invention is to provide a spirometer of high accuracy which is small in size and does not require large expansible chambers to collect the air exhaled from the lungs and which can be used routinely in physical examinations and does not have a sudden blockage of the air being exhaled. It is also an advantage of the present invention to provide embodiments which can be manufactured at a low cost so that patients can obtain spirometers while in the hospital, or even for home use.

The present invention uses a pressure signal analgous to the volume passing through a tube rather than collecting the total volume of air in an expansible chamber, thus eliminating the much larger expansible chamber or clumsy bags, while providing an accurate signal representative of $FEV_1$ and FVC and even of a ratio of $FEV_1$ over the FVC desired. It is intended that the present invention will be used with a simplified chart or nomograph based on sex, age, height of the subject to screen patients to determine who should seek medical help or further testing in a pulmonary testing center.

An aspirator is generally defined as a suction pump operated by the pressure differential created by the high speed flow of a fluid past an intake orifice.

A venturi uses a narrow section in a passageway to increase the velocity of a fluid passing thereby to create a pressure differential between the narrowed section and either side thereof. A venturi is used to measure the flow of fluid.

Flow is the volume of fluid that flows through any given section of a passageway during a unit of time, thus the integral or totaled suction or negative pressure generated by a volume of fluid passing through a passageway across an aspirator orifice is analogous to the total volume passing that point and if a reading is taken at timed intervals, an indication of volume passing through the passageway during a predetermined period of time may be measured.

SUMMARY OF THE INVENTION

An apparatus for testing pulmonary functions is provided having a passageway therethrough having a venturi therein with an aspirator orifice adjacent the venturi. The negative pressure generated at the aspirator orifice by a patient blowing through the passageway is measured over a timed period, as well as for the full exhalation of the patient. The measurement can be accomplished by the raising of a column of colored liquid or by a small expansible chamber working in reverse. Electrical, mechanical and pneumatic timers can be utilized to cut off the aspirator orifice or alternatively to indicate a reading after one second. The aspirator orifice may include a check valve and a release opening to hold the fluid column in position, or alternatively, can use a cut off valve such as a solenoid valve or a gravity or air actuated timer incorporating a permanent magnet to shut off the aspirator opening. Thus, with a small easily handled device, the forced expiratory volume for one second, as well as forced vital capacity, can be easily measured.

BRIEF DESCRIPTION OF THE DRAWINGS

Other objects, features and advantages of the present invention will be apparent from the written description and the drawings, in which.

DESCRIPTION OF THE PREFERRED EMBODIMENTS

Figure 1:
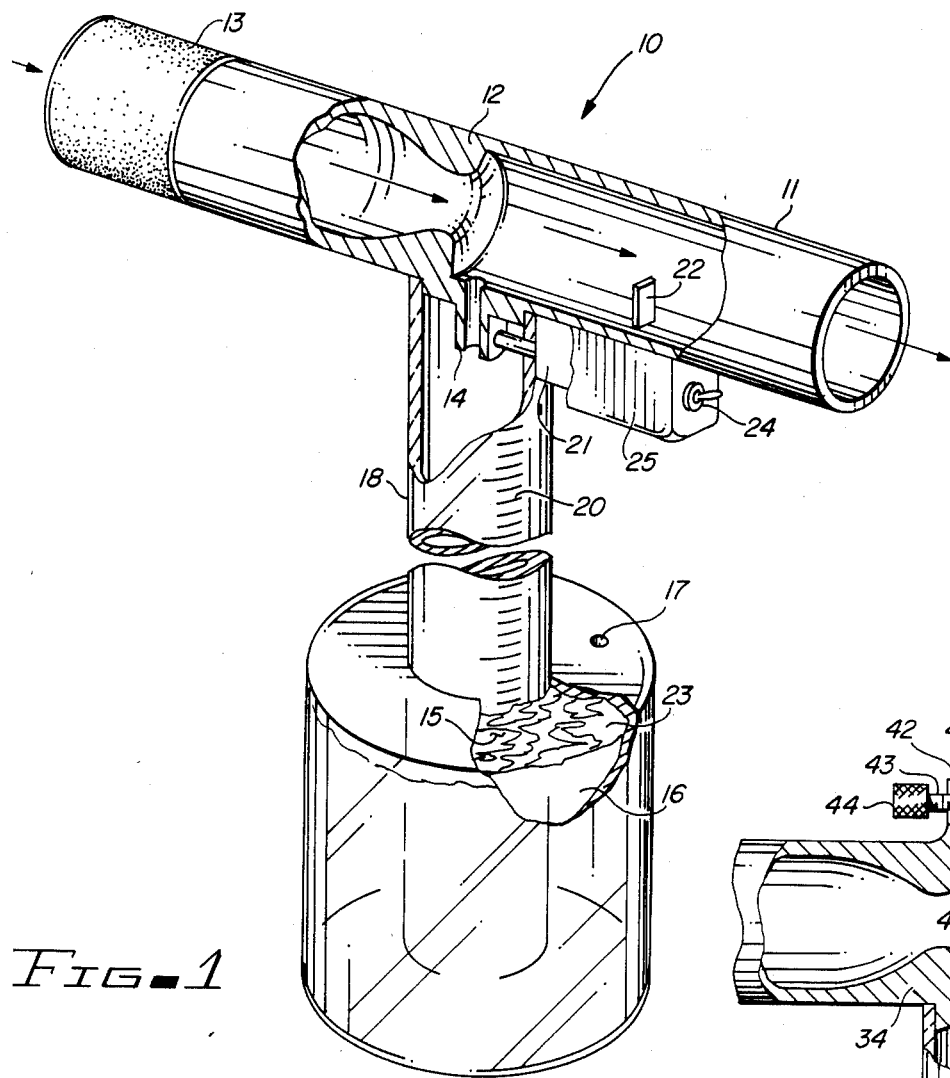
FIG. 1 is a cutaway perspective view of an apparatus for testing pulmonary functions in accordance with the present invention.
Figure 2:
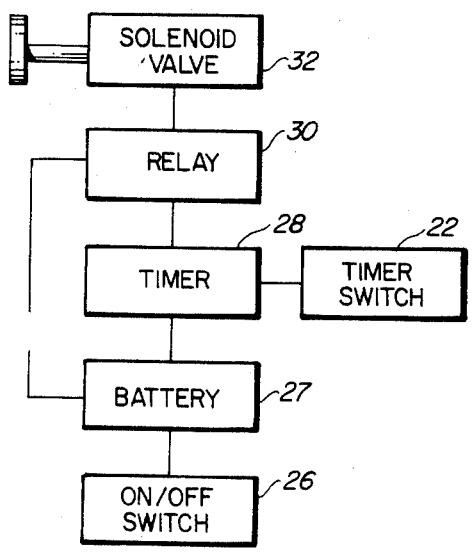
FIG. 2 is a block diagram of an electrical circuit for operating a solenoid valve of the embodiment of FIG. 1.

Referring to FIGS. 1 and 2 of the drawings, a spirometer or apparatus for testing pulmonary functions 10 is illustrated having a tubular passageway 11 having a venturi 12 therein and a replaceable mouth piece 13 mounted to one end of the tube 11. The mouth piece 13 is such that it can be replaced for each patient using the testing apparatus 10. The tube 11 has an aspirator orifice 14 placed adjacent to the venturi 12 on the opposite side of the venturi from the direction of flow of a patient exhaling into the tube 11. Thus, the patient exhaling through the mouth piece 13 and tube 11, will have the velocity of the exhaled air increased by the venturi 11 and will generate a negative pressure at the aspirator orifice 14, which will vary in proportion to the volume of air pushed through the tube 11. A reservoir 15 holds a liquid, such as a colored saline solution 16 therein and has an atmospheric opening 17 in the top thereof and is attached to a column 18 having graduations 20 thereon, so that a patient blowing into the tube 11 creates a negative pressure at the aspirator opening 14 which will raise the liquid 16 in the column 18 in direct proportion to the air being exhaled through the tube 11. In actual testing situations, the patient is directed to fill his lungs and blow through the mouth piece 13 as hard as he can. Inasmuch as the tube 11 is open without any restriction other than the venturi 12, there is little resistance to the flow of air through the tube. The aspirator orifice 14 is formed with a conventional solenoid valve 21, which shuts off the aspirator orifice after a timed period, such as one second, so that the forced expiratory volume in one second ($FEV_1$) can be determined. A timer is initiated by a breath actuated electrical switch 22. Air pressure is applied against the switch surface actuating the switch upon the first exhaled breath striking the switch arm 22. It should be clear, however, that other means for initiating the timer can also be utilized without departing from the spirit and scope of the invention. For instance, a rising column of liquid can push against a small float connected to a piezoelectric crystal to generate a voltage or can contact a galvanic probe having two dissimilar metals separated by an insulator, so that a saline solution contacting the probe generates a voltage. Photocells or other conventional techniques can also be utilized as desired. The system is set and actuated by turning an on/off switch 24 connected to the container 25 which holds the timer, the relay for operating the solenoid, as well as the battery. As can be seen in FIG. 2, the on/off switch is connected to the battery compartment 27 and the timer switch 22 actuates an integrated circuit timer 28, which in turn actuates an electrical relay 30, which uses the large current directly from the battery through line 31 to drive a conventional solenoid valve 32 having a small DC solenoid connected to a valve element. A solenoid valve 32 is spring loaded in one direction and may be a normally closed valve which is opened by turning on the switch 26 and is released by the relay and timer to lock the liquid in its raised position after one second.

Figure 3:
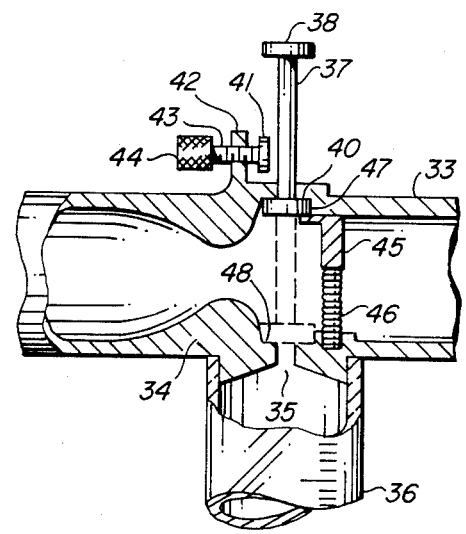
FIG. 3 is a cutaway sectional view of an alternate embodiment of a timing mechanism and cut off valve.

The embodiment in FIG. 3 shows an alternate mechanical timing method for use in connection with a tube 33 having a venturi 34 therein and an aspirator 35 connected to a column 36 similar to the column 18. A sliding rod 37 has a lip 38 on the top thereof and slides in a bushing 40 adjacent a magnet 41 connected to a shaft 43, slid or threaded in bracket 42. Shaft 43 has a small handle 44. The magnet can be positioned to apply a predetermined attraction to the steel rod 37 to vary the rate that the rod falls from the force of gravity. An element 45 is held by a small coil spring 46 to the base of the tube 33 and swings in front of the valve element 47 attached to the steel rod 37 inside the tube 33. Thus, exhaling through the tube 33 will apply a sufficient pressure differential to element 45 to push it out of the way and let the steel rod 37 fall. The valve element 47 may be a permanent magnet which engages a ferrous washer shaped valve element 48 to give a complete seal to the aspirator orifice 35. The magnet 48 holds the opening 35 in a closed position to prevent the column of liquid from returning, so that a reading can be taken of the maximum heighth of the column of liquid raised in column 18. In addition, the negative pressure in the column 35 is not released until the magnet 47 gets very close to the opening 35 at which time the magnet is pulled rapidly to effect a rapid closing to make the one second timing more accurate. In this embodiment, the valve is reset by merely lifting the handle 38 to allow the element 45 to catch the valve element 47.

Figure 4:
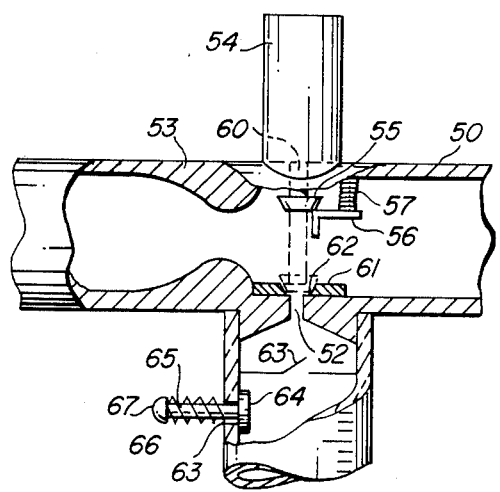
FIG. 4 is a cutaway sectional view of another timing mechanism and cut off valve.

A similar embodiment is illustrated in FIG. 4 having a tube 50 and a column 51 having an aspirator orifice 52 and a venturi 53. In this embodiment, a pneumatic or spring timer 54 is attached to the top of the tube 50 and has a magnetic valve element 55 held by a switch element 56 attached to a small spring 57 mounted from the top of the tube 50. Thus, exhaling through the tube 50 creates an increased velocity through the venturi 53 against the element 56 having a tab 58 holding the valve element 55 to release the valve element of the timer 54 to allow the shaft 60 of the timer to slide down to engage the metal washer portion 61 to allow the magnet 62 to engage and close the aspirator orifice 52. This embodiment has a standard check valve 63 therein for allowing the column of liquid to be raised in the column 51 in only one direction, so that the timer 54 can be disengaged to determine a patient's forced vital capacity or a total volume exhaled over a several second period. However, the column locked by the check valve must be released for the next test and a small opening 63 is covered with valve element 64 connected to a shaft 65 having a spring 66 therearound. Pushing a trigger tab 67 pushes the shaft 66 and valve element 64 around the shaft 65 to release the column of liquid in the column 51. This variation can, of course, be used in connection with the embodiments illustrated in FIGS. 1 and 3, so that those embodiments can also be used to determine the FVC.

Figure 5:
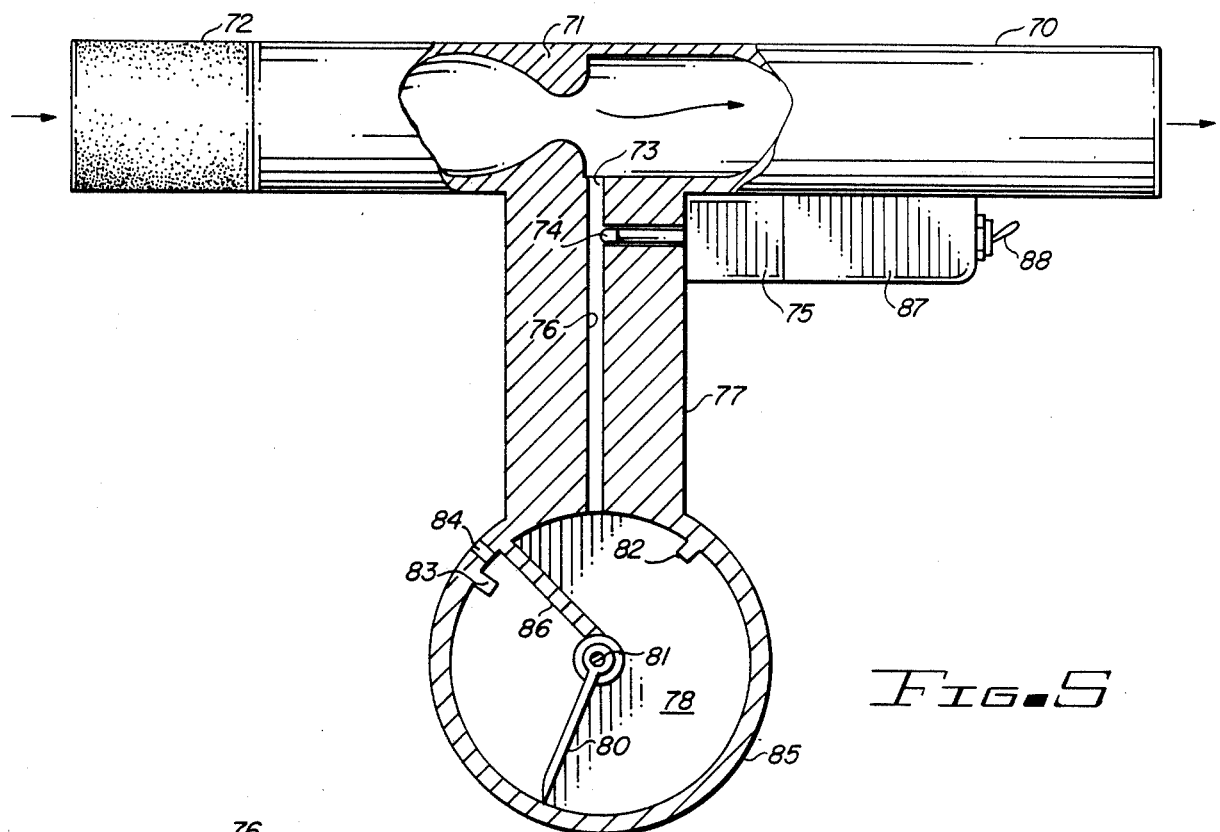
FIG. 5 is a diagrammatic view of a fourth embodiment of an apparatus for testing pulmonary functions in accordance with the present invention.
Figure 6:
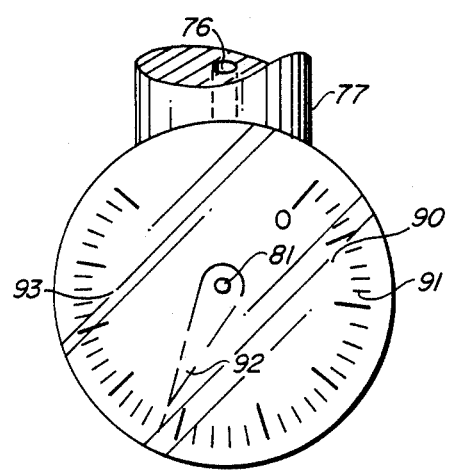
FIG. 6 is a cutaway elevation of the dial portion of the embodiment of FIG. 5.

Turning to FIGS. 5 and 6, an alternate embodiment is illustrated having an exhaling tube 70 having a venturi 71 formed therein and a mouth piece 72 attached to one end. Tube 70 has an aspirator opening 73 formed with a solenoid valve 74 acutated by the solenoid portion 75 and connected to a tube 76 inside a handle 77. The tube opens into an expansible chamber 78 forming a cylindrical shape and having a rotating wiper 80 fixedly attached to a rotating shaft 81. The wiper 80 has a stop 82 for stopping it in one direction and a microswitch stop 83 for stopping it in the opposite direction, as well as an atmospheric opening 84 located behind the wiper 82 relieve any pressure by the rotation of the wiper 80 within the angular wall 85 following the chamber 78. A fixed wall 86 determines the other portion of the chamber, thus exhaling through the tube 70 will generate a negative pressure at the aspirator orifice 73 and in the chamber 78 to thereby draw the wiper 80 and shaft 81 in a rotating action. Continuous blowing through the tube 70 will continue to draw the wiper 80 proportional to the amount of air blown through the tube 70. The unit can be timed for one second with an integrated circuit timer mounted in the housing 87 having an on-/off switch 88, which operates in the same manner as illustrated in FIG. 2, except the timer is acutated by the microswitch stop 83 when the wiper 80 is pulled from the stop upon the initiation of the exhaling into the tube 70.

In FIG. 6, the cover covering the cylindrical container 81 is in place and has a dial 90 having graduations 91 thereon and a needle 92 connected to the shaft 81 to turn with the shaft with the rotation of the wiper 80 to point towards the graduations. A transparent cover 93 covers the gauge 90 and dial 92. The dial is shown connected to the handle 77 with the tube 76 passing therethrough. This embodiment negates the use of liquids, but requires a specially designed expansible chamber, which works in the reverse from a normal expanding chamber by decreasing the volume within the chamber responsive to the flow of air through the tube 70.

Figure 7:
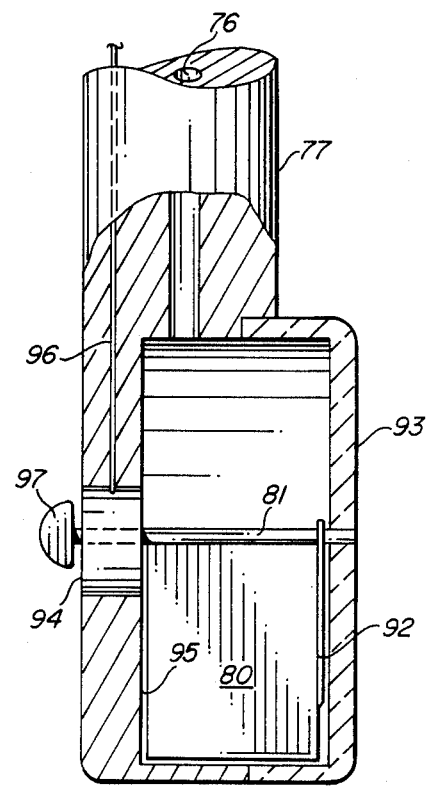
FIG. 7 is a modified sectional view of the apparatus for testing pulmonary functions in accordance with FIGS. 5 and 6 altered to include a potentiometer.

In FIG. 7, the column 77 having the tube 76 therein and the transparent cover 93, needle 92 and shaft 81, along with the wiper 80, operates in the same manner, except for the modification of the addition of a rotary potentiometer 94 mounted to the other end of the shaft 81 from the needle 91. In this embodiment, a false bottom 95 separates the chamber 78 (FIG. 5) and hides the potentiometer 94 which has electrical conductors 96 running therefrom. In addition, the manual return handle 97 is also connected to the shaft 81 in the same manner as would be connected in FIGS. 5 and 6. The rotary potentiometer allows this embodiment to be used in the same manner as illustrated in the embodiments of FIGS. 8 and 9.

Figure 8:
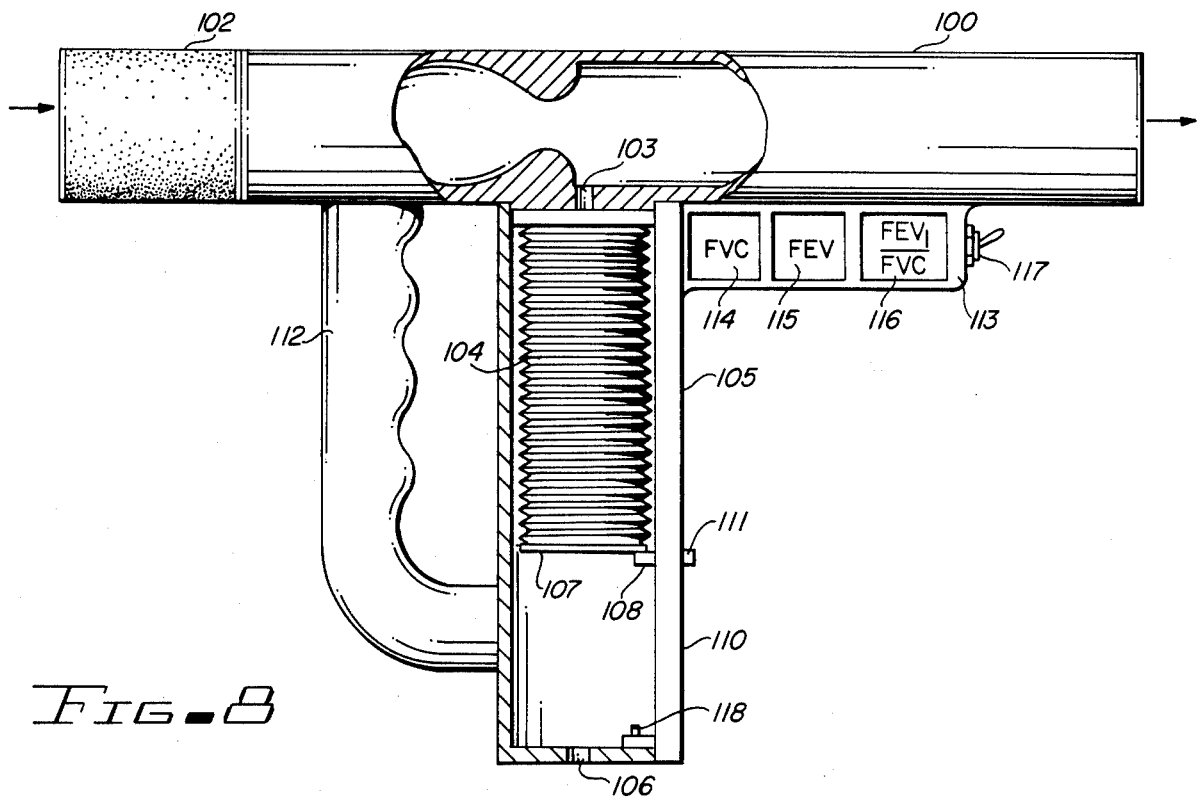
FIG. 8 is a diagrammatic view of yet another embodiment of an apparatus for testing pulmonary functions.
Figure 9:
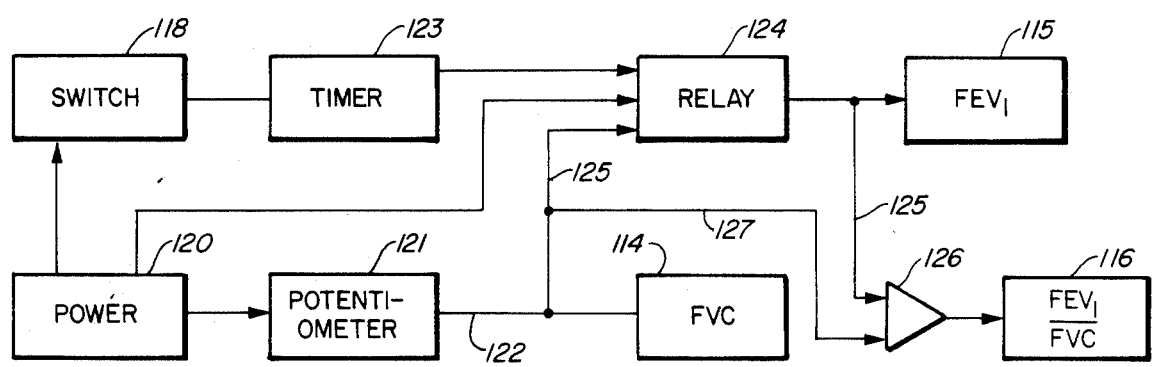
FIG. 9 is a block diagram of an electrical circuit for operation of the embodiments of FIGS. 7 and 8.

Referring to FIGS. 8 and 9, a hollow tube 100 has venturi 101 mounted therein and a mouth piece 102 removably mounted to one end of the tube 100. An aspirator orifice 103 in the tube 100 is adjacent the venturi 101 and opens directly into a small bellows 104. The bellows is inside of a casing 105 and the casing has an opening 106 to atmosphere and has a rigid end 107 connected to a tab 108 which is the sliding tab of a linear potentiometer 110. The potentiometer is wired backwards, so that a DC current passing therethrough has its voltage increased as the tab 108 slides upwards, responsive to the patient exhaling through the tube 100 generating a negative pressure in the opening 103 and in the bellows 104 to raise the bellows. The bellows is returned by return knob 111 extending through the potentiometer 110 to the other side from the tab 108. This embodiment shows a handle 112 for the patient to hold and a housing 113 having three LCD displays thereon. One display 114 gives a reading on the FVC, while the display 115 reads the $FEV_1$ and display 116 reads the $FEV_1$ divided by the FVC ($FEV_1/FVC$). An on/off switch 117 is provided and a microswitch 118 actuates the timing mechanism responsive to the bellows 104, tab 108 being lifted off the microswitch 118. This embodiment works as shown in FIG. 9, by having a power source 120, such as a battery or a rectifier connected to an outlet receptacle. The power is connected through the potentiometer 121, which can be a linear potentiometer as shown in FIG. 8, or a rotary potentiometer as shown in FIG. 7, and which produces a voltage depending upon the position of the potentiometer. The output voltage in line 122 is read by display 114. The display shows voltage signal calibrated to read out a signal analgous to the volume of air passing through the tube in liters or liters per second. The power source is also connected through the switch 118 which is actuated by the beginning of the lifting of the bellows 104, and is connected to an integrated circuit timer 123, which may be a one second timer and actuates a relay 124. The signal from the potentiometer is fed through a line 125 into the relay 124 and into the display 115 so that the display 115 is stopped at the end of one second to give an indication of the $FEV_1$ of the patient. The, signal being fed from relay 124 is also fed through line 125 to a differential amplifier 126 or other dividing circuit, while line 122 is connected through a line 127 from the potentiometer 121 to the other side of the differential amplifier 126. The integrated circuit 126 divides the $FEV_1$ by the FVC to give a display 116. Thus, the $FEV_1$, FVC and $FEV_1/FVC$ can be read simultaneously displayed. It will also be clear that the potentiometer in FIG. 7 will accomplish the same thing as the one in FIG. 8, and that this embodiment eliminates the need for solenoids or other cut offs for the aspirator opening 103, while providing the additional readings of the FVC and the $FEV_1/FVC$ simultaneously with the $FEV_1$ reading.

It should be clear at this point that an apparatus for testing pulmonary functions has been provided which reduces the size of most prior art spirometers capable of measuring the $FEV_1$ by eliminating the large, expansible chambers or bags and complex timing mechanisms and a sudden cut off of the patient's exhaling after one second. It should also be clear, however, that other embodiments are contemplating as being within the scope of the invention. For instance, in FIG. 8, instead of using a potentiometer, other means could be used such as using a magnet on the bellows actuating a series of hall effect switches to indicate a series of stepped levels. It should also be clear that the embodiment in FIG. 5 has a wiper 80 which moves with a uniform frictional resistance, thereby using a linear scale; while the embodiments of FIGS. 1 through 4 lift a column of liquid effectively acts to compress the graduations of the scale since more negative pressure is needed as the column of liquid rises. Different embodiments illustrated in the simpler embodiments can be provided to individual patients, while the use of the embodiment in FIGS. 8 and 9 might be more useful for screening patients during physical examinations.

Figure 10:
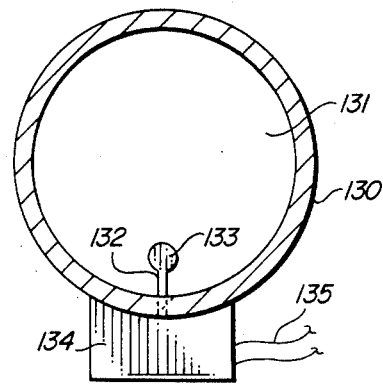
FIG. 10 is a sectional view of the initiating switch for initiating a timer.

In FIG. 10, an alternate embodiment for initiating the timer in connection with the embodiment illustrated in FIGS. 1, 2, 5, 6, 7, 8 and 9, is shown in which a tube 130 having a passageway 131 has a small surface 132 for a patient's exhaled air to be impinged upon to bias the surface 132 and the stem 133 holding surface 132. Stem 133 acts as a lever and extends into a casing 134 having a piezoelectric crystal therein which generates an electrical signal in the wires 135. To actuate the timer, the switch initiator operates in a manner similar to piezoelectric or variable reluctance photo cartridges, which can in fact, be adapted for the switch in the present invention. This embodiment has the advantage that the maximum pressure differential applied to the surface 132 and stem 133 and thus to the piezoelectric crystal can be registered on a display to indicate the peak flow during the exhalation of patients through the passageway 131. Similarly, a variable reluctance pick up with an amplifier can be used in place of the piezoelectric crystal as desired to actuate the switch and to measure the peak flow. In a variable reluctance pick up, the variations in reluctance caused by an armature's movement in a magnetic field or circuit is measured. Advantageously, inexpensive components for photo cartridges or similar equipment can be utilized in casing 134 to reduce manufacturing costs and as used in initial tests.

Accordingly, the present invention is not to be construed as limited to the forms shown, which are to be considered as illustrative rather than restrictive.

We claim:

1. A pulmonary functions testing apparatus comprising in combination:
   a body having a passageway therethrough;
   an aspirator orifice entering said passageway through said body;
   means to measure the volume of air passing through said passageway, said means being responsive to the negative pressure generated at said aspirator orifice, said means to measure the volume of air passing through said passageway including a reverse acting expansible chamber, which chamber reduces its volume in proportion to the volume of air passing through said passageway; and
   indicating means to indicate the volume measured by said measuring means, whereby the volume of gas passing through said passageway can be determined.

2. The apparatus in accordance with claim 1, in which said body has a venturi formed in the passageway therethrough.

3. The apparatus in accordance with claim 2, including timing means for timing the volume of gas passing through said passageway for a predetermined time period.

4. The apparatus in accordance with claim 3, in which said timing means closes said aspirator orifice after a predetermined time period.

5. The apparatus in accordance with claim 3, in which said indicating means has a plurality of displays, one indicating the volume of air passing through said passageway in said body and a second display indicating the volume of air passing through said passageway during the predetermined time period of said timing means.

6. The apparatus in accordance with claim 5, in which said expansible chamber is a bellows.

7. The apparatus in accordance with claim 6, in which said bellows is attached to a linear potentiometer to generate an electrical signal through said potentiometer responsive to the movement of said bellows responding to said aspirator orifice pressure.

8. The apparatus in accordance with claim 7, including a microswitch mounted to indicate the initial movement of said bellows.

9. The apparatus in accordance with claim 8, in which said timing means is an integrated circuit timer actuated by said microswitch to indicate the signal from said potentiometer after a predetermined time period.

10. The apparatus in accordance with claim 9, including a dividing network for dividing the signal from said potentiometer after said predetermined time period by the signal from said potentiometer and displaying the ratio thereof on a third display.

11. The apparatus in accordance with claim 3, in which said expansible chamber includes a cylindrical chamber with a rotating wiper blade for decreasing the volume of said expansible chamber.

12. The apparatus in accordance with claim 11, in which said expansible chamber wiper is attached to a rotating shaft attached to a dial outside of said expansible chamber to move said wiper across a gauge surface having graduations thereon.

13. The apparatus in accordance with claim 12, in which said aspirator orifice is connected through a solenoid valve adapted to shut off said orifice upon actuation of said solenoid.

14. The apparatus in accordance with claim 13, in which said solenoid valve is actuated by a relay responsive to an electric timer.

15. The apparatus in accordance with claim 14, including an on/off switch.

16. The apparatus in accordance with claim 15, in which said cylindrical expansible chamber having a wiper therein has a fixed wall portion and an opening therein behind wiper to open said chamber to atmosphere behind said rotating wiper.

17. The apparatus in accordance with claim 16, in which a microswitch is mounted in said cylindrical chamber to indicate initial movement of said wiper.

18. The apparatus in accordance with claim 16, including means for returning said wiper to starting position.

19. The apparatus in accordance with claim 11, in which said wiper blade is attached to a shaft and said shaft is attached to a rotary potentiometer on one end for generating a signal responsive to the rotation of said wiper.

20. The apparatus in accordance with claim 2, in which said aspirator orifice is connected to a transparent column extending into a fluid reservoir, whereby the fluid is drawn into said column responsive to the negative pressure generated at said aspirator orifice.

21. The apparatus in accordance with claim 20, having timing means for shutting off said aspirator orifice after a predetermined time period.

22. The apparatus in accordance with claim 21, in which said timing means includes a solenoid valve for cutting off said aspirator orifice after a predetermined time period.

23. The apparatus in accordance with claim 22, in which said solenoid valve is actuated by an electronic timer actuating a relay to actuate said solenoid.

24. The apparatus in accordance with claim 23, including means for starting said timer upon a patient blowing through said passageway.

25. The apparatus in accordance with claim 24, in which said means for actuating said timer includes a galvanic probe having spaced electrodes of different metals positioned directly over said liquid in said column for generating an electrical signal on contact with the rising liquid in said column.

26. The apparatus in accordance with claim 20, including a check valve mounted in said column to hold said column of liquid in a raised position.

27. The apparatus in accordance with claim 26, in which a relief valve allows the opening of atmosphere in said column to release said column of liquid.

28. The apparatus in accordance with claim 2, having timing means for shutting off said aspirator orifice after a predetermined time period.

29. The apparatus in accordance with wlth claim 28, in which said timing means includes a valve element driven from the opposite side of said aspirator orifice to close said aspirator orifice.

30. The apparatus in accordance with claim 29, in which said valve element has a permanent magnet portion for holding said valve element to a metal portion adjacent said aspirator orifice.

31. The apparatus in accordance with claim 30, in which said valve element is attached to an elongated rod which is gravity dropped to close said aspirator orifice.

32. The apparatus in accordance with claim 31, in which an actuating element is flexibly attached in said passageway to hold said valve element until a patient breaths through said body passageway to thereby start the timing for the dropping valve element.

33. The apparatus in accordance with claim 32, in which a magnet is positioned a predetermined distance from said elongated metal rod for dropping the metal rod at a predetermined timing rate.

34. The apparatus in accordance with claim 33, in which said magnet is adjustable to vary the closing time for said valve element.

35. The apparatus in accordance with claim 29, in which a solenoid is mounted to said body across said passageway from said aspirator orifice and is actuated by a timer for actuating said solenoid to close said aspirator orifice after a predetermined timing cycle.

36. The apparatus in accordance with claim 1, in which said body has a handle thereon for holding said apparatus.

37. The apparatus in accordance with claim 36, in which said body has a removable mouth piece removably attached thereto for readily changing the mouth piece for different patients.

38. The apparatus in accordance with claim 1, in which a small surface is attached to a stem and protrudes into the passageway of said body and the stem is attached to an electrical generating means generating an electrical signal indicative of the pressure applied against the surface indicative of the peak flow through said passageway.

39. The apparatus in accordance with claim 38, in which said stem is attached to vary the pressure on a piezoelectric crystal generating a signal responsive to the pressure on said plate and a display means displays the maximum signal generated by said piezoelectric crystal.

40. A pulmonary functions testing apparatus comprising in combination:
a body having a passageway therethrough and a venturi formed in the passageway thereof;
an aspirator orifice opening into said passageway through the wall thereof adjacent said venturi;
measuring means to measure the volume of gas passing through said tube responsive to the pressure generated at said aspirator orifice, said means including a reverse acting expansible chamber actuated by negative pressure at said actuator orifice upon a patient breathing through said passageway; and
timing means for timing the volume of gas passing through said passageway for a predetermined time period, whereby said measuring means indicates the volume of gas passing through said passageway during said predetermined timed period.

41. The apparatus in accordance with claim 40, including at least one display for displaying the measurement of said measuring means.

42. The apparatus in accordance with claim 40, in which said display means includes a plurality of displays for displaying total volume of a patient's breathing through said passageway of said body and said volume after a predetermined time period.

43. The apparatus in accordance with claim 42, in which said reverse acting expansible chamber generates an electrical signal responsive to changing volume of the chamber, which signal is displayed after a predetermined time period and after completion of a patient exhaling through said body's passageway.

44. The apparatus in accordance with claim 43, including dividing means for dividing the electrical signal after a predetermined time period by a signal following the total exhalation of a patient.

45. The apparatus in accordance with claim 40, in which said timing means includes a mechanical timing means for closing said aspirator orifice after a predetermined time period.

46. The apparatus in accordance with claim 40, in which said timing means includes an electric solenoid for closing the aspirator orifice after a predetermined time period.

47. The apparatus in accordance with claim 46, in which said electric solenoid is actuated by an electronic timer to close said aspirator orifice after a predetermined time period.

48. The apparatus in accordance with claim 47, includes an actuating switch for actuating the beginning of a timing period upon a patient beginning the exhalation through the passageway of said body.

49. The apparatus in accordance with claim 48, in which said actuating switch includes a surface protruding into the passageway of said body and connected to an electrical signal generator for generating an electrical signal upon pressure being applied upon said surface in said passageway.

50. The apparatus in accordance with claim 49, in which said signal generator includes a piezoelectric crystal in which the pressure on said surface by the exhalation of a patient through said passageway initiates an electrical signal starting said timing means.

* * * * *